United States Patent [19]
Schwartz et al.

[11] Patent Number: 5,690,632
[45] Date of Patent: Nov. 25, 1997

[54] OSTEOSYNTHESIS SCREW FASTENER HAVING ANGULARLY ADJUSTABLE THREADS AND METHODS OF USE THEREFOR

[76] Inventors: Paul Steven Schwartz, 19 El Rincon, Orinda, Calif. 94563; Jerry K. Erben, 132 Fountainhead Ct., Martinez, Calif. 94553

[21] Appl. No.: 568,313

[22] Filed: Nov. 30, 1995

[51] Int. Cl.⁶ .................................................. A61B 17/84
[52] U.S. Cl. ........................... 606/73; 411/429; 411/433
[58] Field of Search ........................ 606/64, 65, 66, 606/72, 73; 411/429, 432, 433, 379, 380, 381, 382, 537

[56] References Cited

U.S. PATENT DOCUMENTS

| | | | |
|---|---|---|---|
| 1,077,049 | 10/1913 | Dodds | 411/379 |
| 1,111,691 | 9/1914 | Flannery | 411/380 |
| 2,489,870 | 11/1949 | Dzus | 128/92 |
| 4,232,497 | 11/1980 | Meschnig | 52/506 |
| 4,971,497 | 11/1990 | Stoffer et al. | 411/108 |
| 5,064,325 | 11/1991 | McRoskey | 411/368 |
| 5,127,914 | 7/1992 | Calderale et al. | 606/65 |
| 5,269,784 | 12/1993 | Mast | 606/69 |

*Primary Examiner*—Michael Buiz
*Assistant Examiner*—David O. Reip
*Attorney, Agent, or Firm*—Sheridan Ross P.C.

[57] ABSTRACT

An osteosynthetic screw fastener and method of using such fastener is disclosed. When threaded onto an end of a bone screw for securing the screw to fractured bone, the fastener has a bone contacting surface that is alignable, independently of the orientation of the screw shaft, with an orientation of the bone surface adjacent to where the screw shaft exits the bone. The independent alignment of the fastener with the bone surface is due to a ball and socket configuration wherein the ball portion includes a spherical threaded nut and the socket is a cavity within the fastener for retaining the spherical nut. Accordingly, the fastener has an access to a threaded bore of the spherical nut so that the screw shaft can be threaded into the bore and secure the fastener against the bone. Additionally, the fastener's bone contacting surface is relatively large with projections thereon that secure the fastener in a desired orientation on the bone and thereby inhibit the fastener from shifting.

16 Claims, 4 Drawing Sheets

5,690,632

OSTEOSYNTHESIS SCREW FASTENER HAVING ANGULARLY ADJUSTABLE THREADS AND METHODS OF USE THEREFOR

FIELD OF THE INVENTION

The present invention relates to osteosynthetic screw fasteners and, in particular, to an osteosynthetic screw fastener that when threaded onto a bone screw shaft that is in a non-normal angular orientation to the bone surface, the osteosynthetic screw fastener can align itself with the bone surface and fixedly seat in a desired position.

BACKGROUND OF THE INVENTION

In osteosynthesis various devices are used for bone fracture alignment and compression. For many bone fractures, bone screws can be threaded into the bone fragments so that the threads grip each of the bone fragments and thereby secure them together for proper healing. Thus, the threaded bone gripping end of the bone screw is commonly embedded within one of the bone fragments. For some bone fractures, however, reliance on bone screw threads solely to maintain bone fragment alignment may pose difficulties in that the screw may be ineffective or the patient may require extended convalescence. Typically, such difficulties are due to a failure of the bone screw to adequately grip one or more bone fragments when stress is applied at the fracture site once the bone screw has been inserted into the bone fragments. A lack of bone hardness is a contributing factor in a substantial number of such failures. That is, one or more of the bone fragments are too soft for the bone screw threads to adequately grip such fragments and, thus, the induced mating threads within the bone fragments become stripped under stress.

In an attempt to alleviate some of the above bone fracture compression failures, bone screws have been inserted to protrude through the bone fragments so that a bone screw fastener can be secured to the threaded end. Such a procedure, however, presents other difficulties. In particular, the threaded screw end may not be in a normal orientation to the bone surface from which it protrudes. Thus, a fastener having a bone contacting surface that is fixedly oriented relative to the bone screw shaft will not properly seat against the bone. Further, if the bone surface contacting the bone screw fastener is soft, then the fastener and/or the bone screw shaft may shift due to the non-normal orientation of the screw shaft relative to the surface contacted by the fastener. Said another way, a tensioning of such a fastener onto a bone screw shaft at a non-normal orientation to the surface of the bone induces a force on both the shaft and the fastener that is parallel to the surface of the bone, thus resulting in a shift of the fastener along the surface of the bone.

Thus, it would be desirable to have a bone screw fastener that alleviates the above-mentioned difficulties.

SUMMARY OF THE INVENTION

The present invention is a bone screw fastener which, when threaded onto a bone screw shaft, is capable of both:

(1.1) seating onto a bone surface, wherein the orientation between the bone surface and the bone screw shaft may be any orientation within a wide range of angular orientations; and (1.2) resisting stresses induced by compression against the bone surface that urge the fastener to shift position on the bone surface when the bone screw shaft is in a non-normal angular orientation to the bone surface.

In providing (1.1) above, it is an aspect of the present invention to include a bone contacting or attachment surface that is orientable to the bone surface to which it is desired that the fastener seat. Thus, even though the bone screw fastener of the present invention may have a substantially different orientation from the bone surface when initially threaded onto the end of the bone screw shaft, as the fastener is threaded further onto the shaft and contacts the bone surface, the fastener aligns with the bone surface.

It is a further aspect of the present invention that for orienting the above-mentioned attachment surface to the bone surface, the present invention includes a ball and socket configuration wherein the ball portion includes a substantially spherically shaped threaded nut that is orientable and entrapped within a socket cavity provided in a housing of the fastener.

In providing (1.2) above, it is an aspect of the present invention to resist such shifting by both having a disproportionately large bone attachment surface in comparison to the size of the fastener, and in addition, having bone gripping projections mounted on the attachment surface. Thus, the bone attachment surface of the present invention is effective in inhibiting the shifting of the fastener that could potentially occur when, for example, (a) there is a non-orthogonal orientation of the bone screw shaft to the adjacent bone surface upon which the screw fastener seats and/or (b) this adjacent bone surface is relatively soft.

The present invention also relates to a method for securing bone surfaces together using a fastener having a rotatable threaded nut that allows orientation of a bone screw shaft with the threaded nut, thus achieving non-orthogonal orientation of the bone screw shaft to the adjacent bone surface upon which the screw fastener is seated.

Other features and benefits of the present invention will become apparent from the detailed description with the accompanying FIGURES contained hereinafter.

DETAILED DESCRIPTION

Figure 1:
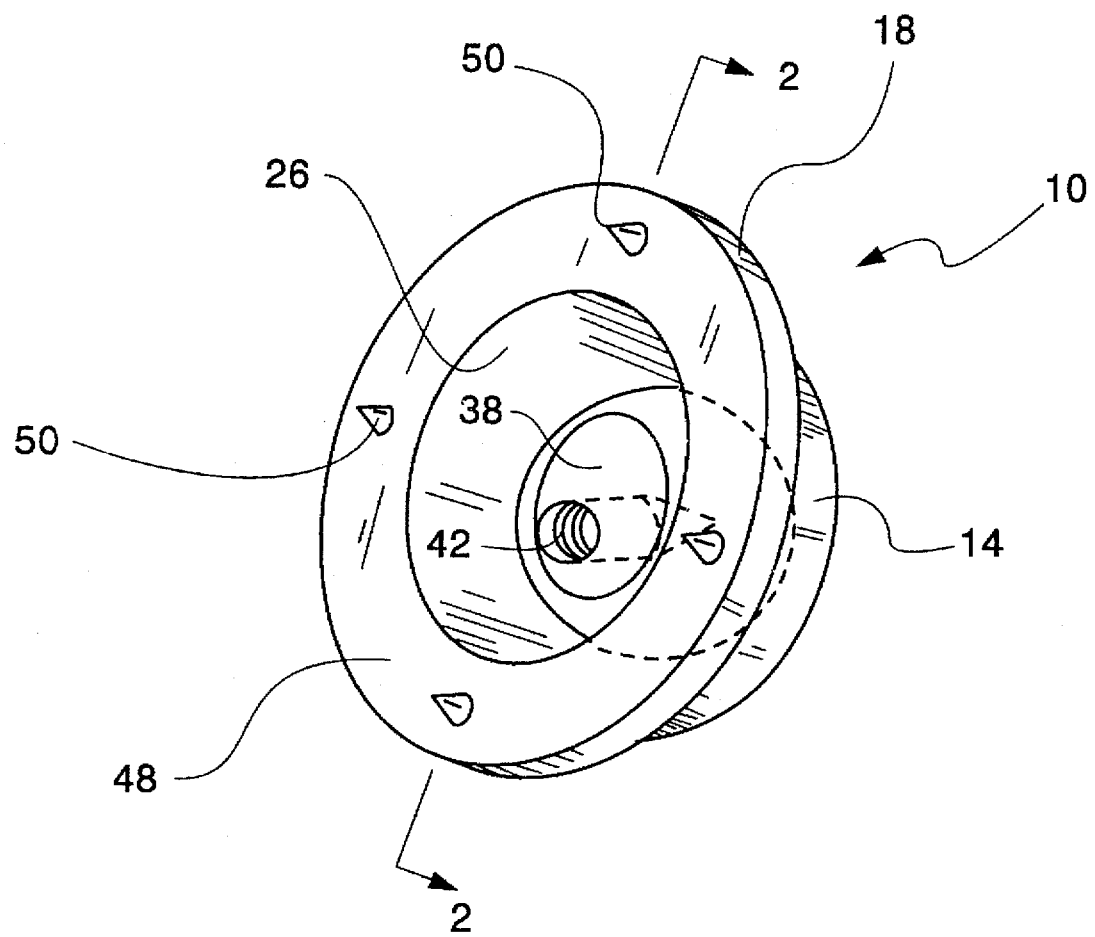
FIG. 1 is a perspective view of the osteosynthetic screw fastener 10 of the present invention wherein the annular attachment surface 48 for attaching the screw fastener to a bone surface is in full view.
Figure 2:
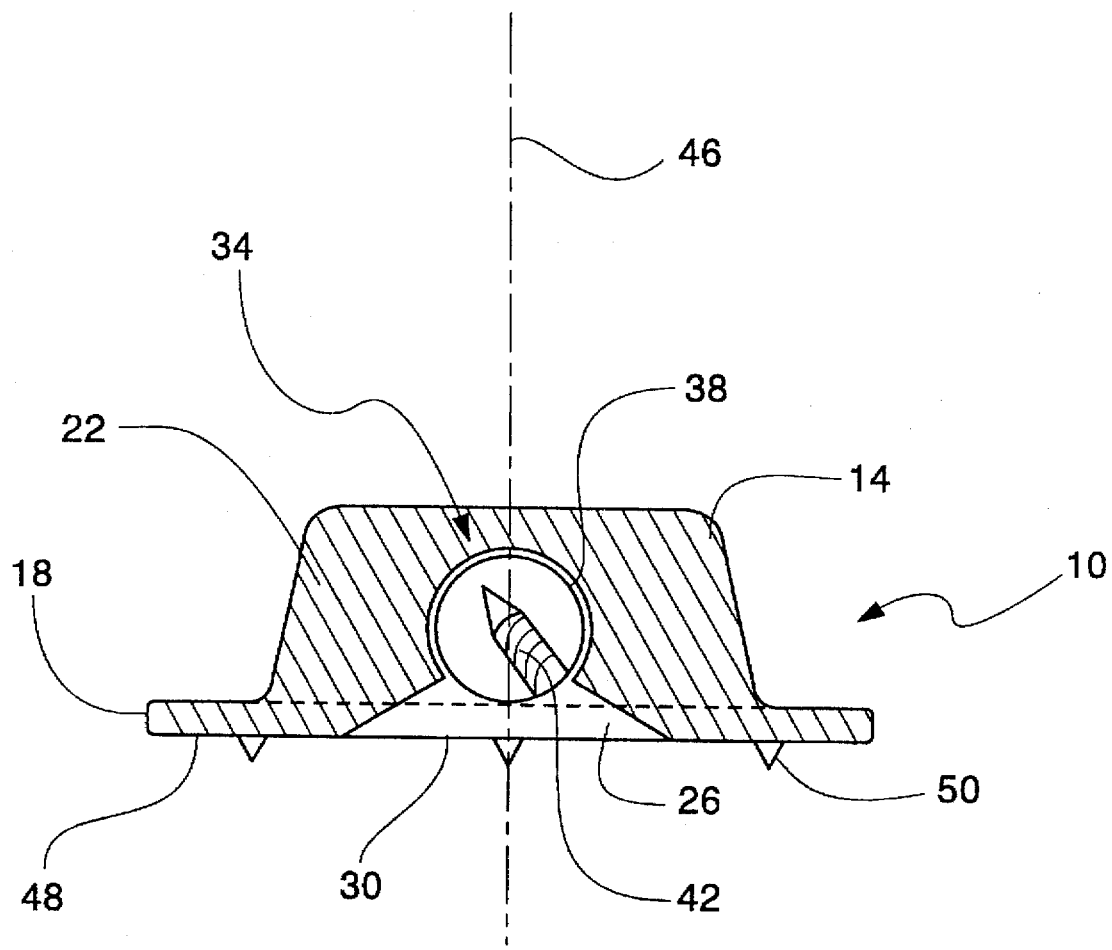
FIG. 2 is a cross-section of the osteosynthetic screw fastener 10 wherein the cross-section is that portion of the fastener 10 which is viewable according to the line of sight arrows 2 of FIG. 1.
Figure 3:
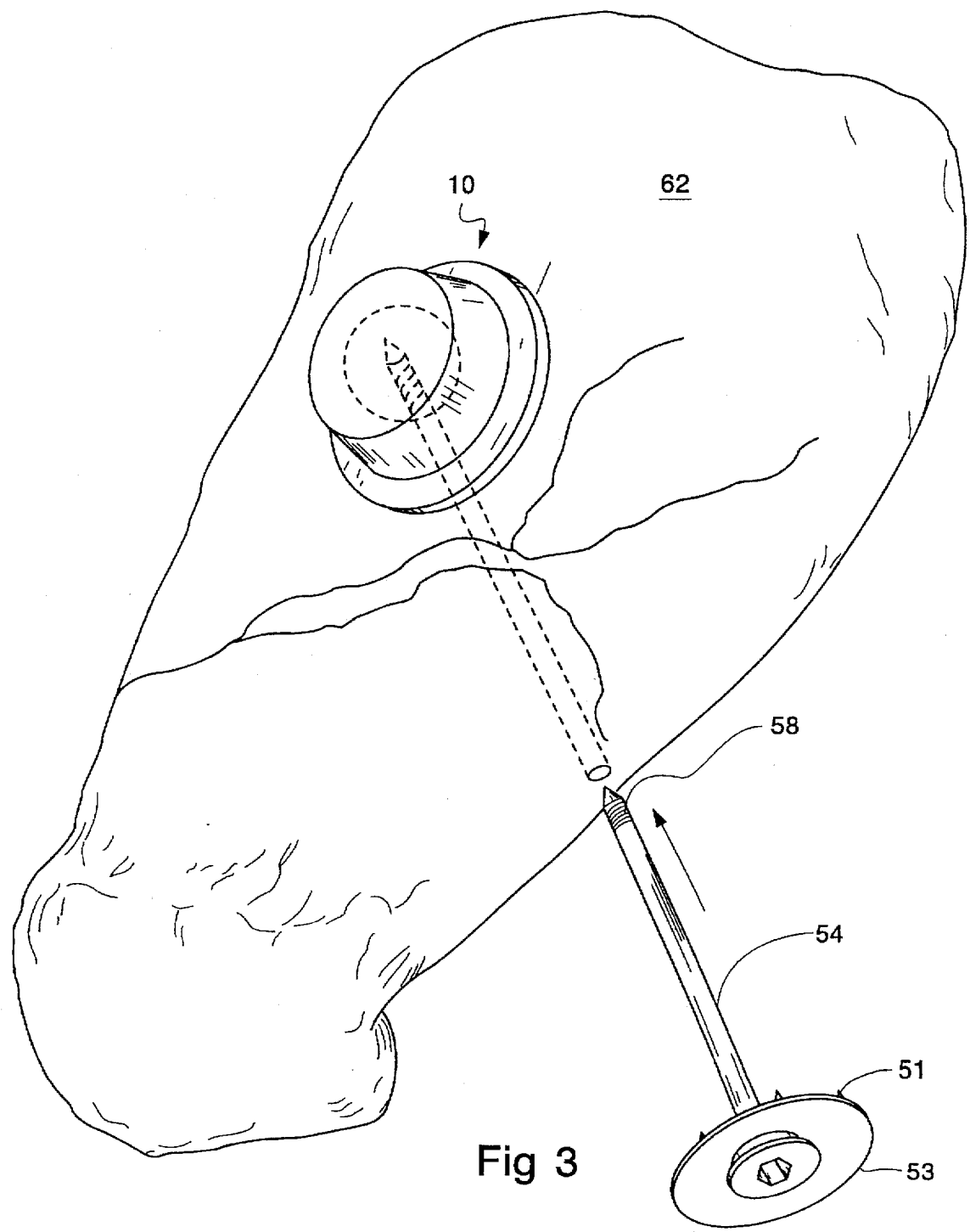
FIG. 3 illustrates how the screw fastener of the present invention may be angularly oriented upon a bone 62 when threaded onto a bone screw 54.

In FIGS. 1-3, the osteosynthetic screw fastener 10 of the present invention is shown in various views. The screw fastener 10 has an external housing 14 which includes a contact ring 18 and a bolt retainer 22 fixedly attached to the contact ring 18. As shown best in FIGS. 1 and 2, the housing 14 has an interior chamber 26 with an opening 30 through the center of the contact ring 18. Additionally, the interior chamber 26 provides, in the present embodiment, a spherical chamber portion 34 whose interior is configured to receive and retain a spherical nut 38. Note that the spherical nut 38 has a threaded bore 42 whose axis 46 is coincident with a diameter of the spherical nut 38. Further note that the use of the term "spherical" shall be understood to encompass embodiments where the rotatable threaded portion comprises curved surfaces. Further note that the interior chamber 26, or more particularly the spherical chamber portion 34, provides a substantially snug fit for retaining the spherical nut 38 within the housing 14. In fact, the spherical chamber portion 34 is contoured so that the spherical nut 38 will only disengage from the spherical chamber portion and exit through the opening 30 by a forcible deformation of the spherical chamber portion or the spherical nut. Additionally, note that it is within the scope of the present invention to provide other means for adjustably securing such a spherical nut 38 within the housing 14, such as with projections or pegs (not shown).

Referring once again to the contact ring 18, this ring has an attachment surface 48 which is the surface that contacts a bone (e.g., bone 62, FIG. 3) and acts as the anchor or fastening end to a bone screw 54 that has been inserted through the bone 62. Note that in order to assure that the screw fastener 10 remains in position, the attachment surface 48 can include gripping projections 50 that inhibit the screw fastener 10 from sliding from a desired position on a bone.

As can be seen in both FIGS. 1 and 3, the spherical nut 38 is adjustable within the spherical chamber portion 34 so that the threaded bore 42 may be oriented in a plurality of angles relative to the substantially planar attachment surface 48. Thus, a bone screw 54 having a threaded bone insertion end 58 may be inserted through a bone (e.g., bone 62) and exit an opposite side of the bone at an acute angle to the bone surface wherein the bone screw end 58 can be threaded into the spherical nut 38. As shown in FIG. 3, the bone screw has an opposite end fitted with a washer 53 having prongs 51 thereon to assist in securing the screw 54 once it is tightened against the bone. Since the spherical nut 38 can be angularly adjusted so that the threaded bore 42 is aligned to the same angle as the screw end 58 when it exits the bone 62, the screw fastener 10 may be fastened to the screw end 58 so that an orientation of the attachment surface 48 to the threaded screw end 58 is substantially non-orthogonal.

Note that when securing the screw end 58 in the threaded bore 42, the spherical nut 38 cannot easily rotate about the axis 46 due: (a) to the snugness of spherical nut 38 within the spherical chamber portion 34; and (b) to a high coefficient of friction between the material for the spherical nut and the material for the spherical chamber (as one skilled in the art will understand). The spherical nut 38 should preferably be able to move into proper alignment with a screw 54 but should have its rotational movement restricted once such alignment is achieved. Thus, when threading the screw end 58 into the spherical nut 38, the spherical nut will not be prone to rotate about axis 46 during the threading. Additionally, it is within the scope of the present invention to provide other features for inhibiting rotation of the spherical nut 38. In particular, undesired rotation of the nut can be achieved by fixing the spherical orientation of the threaded nut once it is in proper alignment with the screw using mechanical means. For instance, a peg (not shown) can be inserted through an aperture (not shown) in the housing 14 to contact the spherical surface of the threaded nut 10, thereby maintaining a desired orientation thereof.

In one embodiment, the gripping projections 50 along with the relatively large surface area of the attachment surface 48 inhibit the screw fastener 10 from shifting from a preferred position. That is, there is sufficient frictional contact with the surface of the bone 62 so that even if the screw fastener 10 is threaded tightly onto screw end 58 at an angle substantially different from 90° with the bone surface, the screw fastener 10 will remain in place. In particular, it is believed that a fastener of the present invention having, for example, a diameter of 2 mm will seat more firmly to a bone surface than two more conventional fasteners having diameters up to 4 mm.

Figure 4:
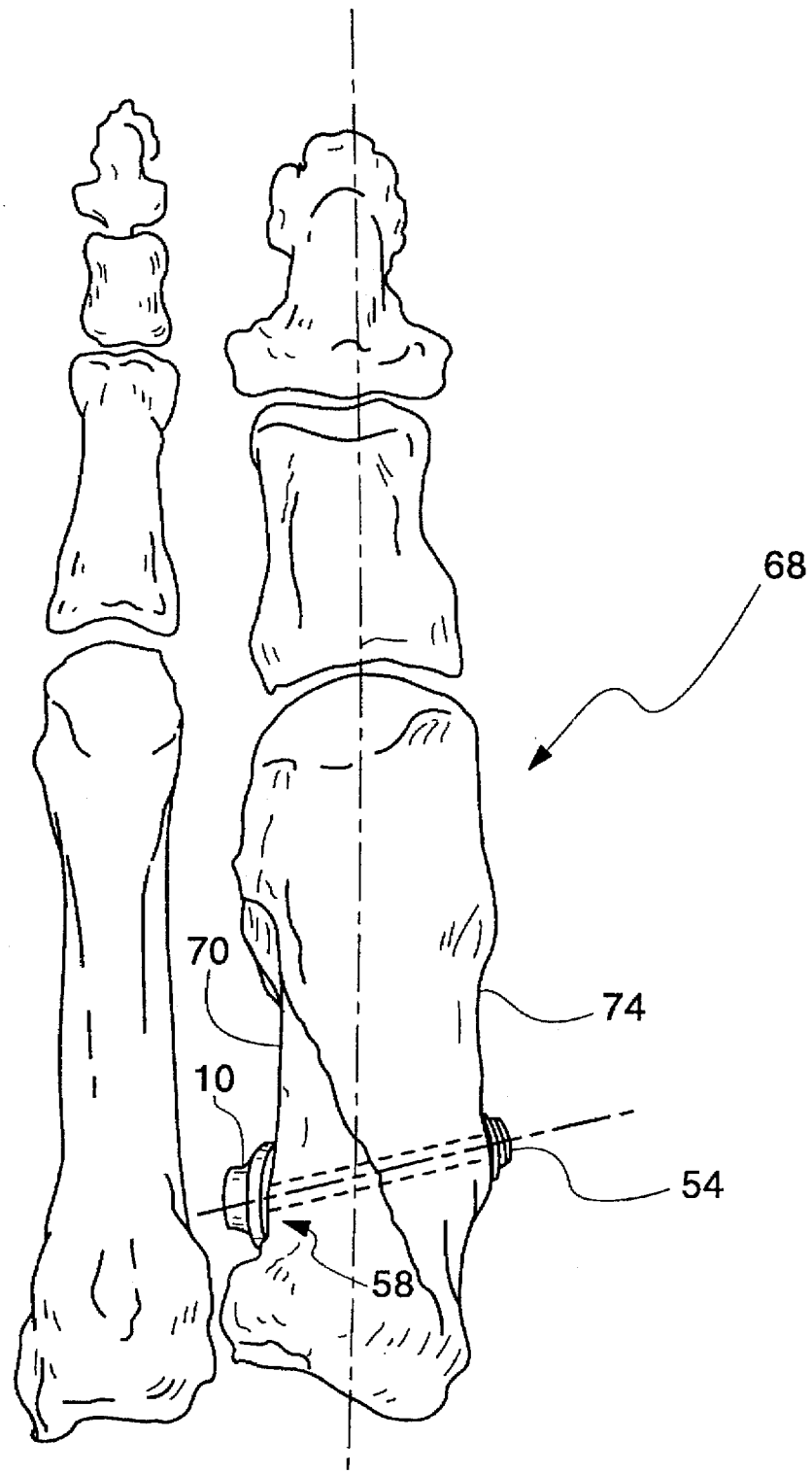
FIG. 4 illustrates the use of the bone screw fastener 10 of the present invention for stabilizing a fracture of the first metatarsal.

In operation one particularly advantageous utilization of the present invention is for closing a base wedge osteotomy of the first metatarsal 68 as illustrated in FIG. 4. The cortical bone on the lateral aspect 70 of the base of the first metatarsal 68 is typically thinner and softer than the medial cortex 74. Thus, bone screw 54 fixation merely by screw threads in the lateral aspect 70 often fails because the threads may not be securely received within the bone. Further, typical bone screw fasteners for threading onto the screw end 58 may also be problematic in that a bone screw provided at an angle may be offset substantially from perpendicular to the bone surface and, therefore, may not adequately anchor the screw.

To avoid these difficulties, the relatively large area of the attachment surface 48 together with the gripping projections 50 provide a stable anchoring of the bone screw to the lateral aspect 70 even if the screw end 58 pierces the bone at a substantially non-orthogonal angle. Thus, utilization of the present invention as in FIG. 4 is believed to provide much stronger fracture compression and better fracture stabilization than fasteners with larger diameters. That is, a fastener 10 having a diameter across the contact ring 18 of no more than 2 mm stabilizes the fracture more effectively than fasteners having diameters of 3–4 mm. Further, it is believed that the present invention provides better first metatarsal stabilization than can be obtained with two typical bone screws secured without fasteners.

Another aspect of the present invention relates to a method for securing an osteosynthetic screw using the fastener of the present invention. The method includes providing a bone contacting or attachment surface that is orientable to the bone surface such that, as the fastener is threaded onto a threaded shaft, the fastener aligns itself with the bone surface. In a preferred embodiment, the present method involves the use of a ball and socket configuration where the ball portion includes a substantially curved shape threaded nut that is orientable within a socket cavity provided in a housing of the fastener. A hole is typically drilled through the desired portion of bone through which a threaded screw is passed. The threaded screw is contacted with the fastener 10 in such a manner that the tip of the screw contacts the opening 30 of the housing 14, such opening preferably being curved or slanted so as to direct the tip of the threaded screw into a threaded aperture of the spherical nut 38. The threaded screw is then rotated to threadably engage the spherical nut, such tightening causing the attachment surface 48 of the contact ring 18 to align with the surface of the bone.

The present invention can be constructed from a variety of suitable materials known to those of skill in the art, such as hardened plastic, metal, and other composite materials having sufficient strength characteristics, coefficients of friction, weight and durability characteristics, etc.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiment described hereinabove is further intended to explain the best mode presently known of practicing the invention and to enable others skilled in the art to utilize the invention as such, or in other embodiments, and with the various modifications required by their particular application or uses of the invention. Finally, although the present invention is principally designed for use in the medical context, it is also contemplated that other non-medical applications could benefit from the present invention (i.e., construction industry, etc.). It is intended that the appended claims be construed to include alternative embodiments to the extent permitted by the prior art.

What is claimed is:

1. A screw fastener, comprising:

a housing having: (a) an interior chamber and; (b) an exterior surface, said exterior surface provided for contacting a fastener attachment surface;

a threaded means provided within said interior chamber, said threaded means having a threaded bore which is closed at one end and which is configured to receive a threaded portion of a screw to threadably secure said screw fastener on said screw, wherein said threaded means has a high coefficient of friction with respect to said interior chamber to prevent undesired rotational movement of said threaded means; and means for resisting a separation of said housing and said threaded means;

wherein said threaded means is adjustable, relative to said housing, for receiving said threaded screw portion at a plurality of angles.

2. An apparatus as claimed in claim 1, wherein the attachment surface includes bone.

3. An apparatus as claimed in claim 1, wherein each said angle of said plurality of angles is determined relative to said housing exterior surface.

4. An apparatus as claimed in claim 1, wherein said threaded means has a rounded outer shape.

5. An apparatus as claimed in claim 1, wherein said interior chamber of said housing has a spherical shape.

6. An apparatus as claimed in claim 1, wherein said housing substantially encapsulates said threaded means.

7. An apparatus as claimed in claim 1, wherein said interior chamber has an opening through said housing exterior surface.

8. An apparatus as claimed in claim 1, wherein said exterior surface includes a gripping means for gripping the attachment surface, thereby inhibiting movement of said housing relative to the attachment surface.

9. An apparatus as claimed in claim 8, wherein said gripping means includes a plurality of projections projecting away from said housing exterior surface and substantially toward the attachment surface.

10. An apparatus as claimed in claim 1, wherein said means for resisting a separation includes a surface of said interior chamber substantially surrounding said threaded means.

11. An osteosynthetic fastener, comprising:

a housing having: (a) an interior chamber; and (b) an exterior surface with an opening to said interior chamber, said exterior surface being for contacting a fastener attachment surface; and an attachment means having a threaded bore which is closed at one end and which is configured to receive a bone setting shaft, said attachment means having an outer surface and being secured in said interior chamber so that the bone setting shaft is received through said opening at any one of a plurality of orientations relative to said exterior surface, said outer surface of said attachment means conforming to the shape of said interior chamber such that said attachment means cannot easily rotate about an axis, whereby attaching said attaching means to the bone setting shaft secures said housing against the attachment surface.

12. An apparatus as claimed in claim 11, wherein said bone setting shaft is threaded.

13. An apparatus as claimed in claim 11, wherein said attachment means has a coefficient of friction with respect to said housing interior chamber to prevent said attachment means from undesired rotational movement.

14. An osteosynthetic fastener, comprising:

a housing having an interior spherical chamber with an opening to an exterior of said housing, said opening capable of receiving a bone securing shaft at a plurality of angles;

a substantially spherical shaft attaching means for attaching to the bone securing shaft at any one of said plurality of angles, said shaft attaching means having a threaded bore which is closed at one end;

wherein said shaft attaching means is mounted in said interior spherical chamber so that attaching said attaching means to the bone securing shaft also attaches said housing to the bone securing shaft.

15. An osteosynthetic fastener as set forth in claim 14, wherein said spherical shaft attaching means is inhibited from rotation once said bone securing shaft is received in said threaded bore.

16. A method for securing bone fractures, comprising:

providing a hole through bone material through which a threaded screw can pass;

inserting a threaded screw through said opening;

engaging said threaded screw with a screw fastener capable of engaging said threaded screw, said screw fastener comprising:

a housing having an interior chamber and an exterior surface; and a threaded means having an outer surface positioned within said interior chamber, said threaded means having a threaded bore which is closed at one end and which is configured to receive a threaded portion of a screw to threadably secure said screw fastener on said screw, said threaded means being adjustable relative to said housing for receiving said threaded screw portion at a plurality of angles, wherein the shape of said outer surface of said threaded means conforms to the shape of said interior chamber such that substantially the entirety said outer surface of said threaded means has a high coefficient friction with respect to said interior chamber to prevent undesired rotational movement.

* * * * *